United States Patent
Maruta et al.

(10) Patent No.: US 9,562,868 B2
(45) Date of Patent: Feb. 7, 2017

(54) COMBUSTION EXPERIMENTAL APPARATUS

(75) Inventors: Kaoru Maruta, Sendai (JP); Hisashi Nakamura, Sendai (JP); Soichiro Kato, Tokyo (JP); Naoki Oikawa, Tokyo (JP)

(73) Assignees: TOHOKU UNIVERSITY (JP); IHI CORPORATION (JP)

( * ) Notice: Subject to any disclaimer, the term of this patent is extended or adjusted under 35 U.S.C. 154(b) by 667 days.

(21) Appl. No.: 13/885,430

(22) PCT Filed: Nov. 18, 2011

(86) PCT No.: PCT/JP2011/076681
§ 371 (c)(1),
(2), (4) Date: May 15, 2013

(87) PCT Pub. No.: WO2012/067233
PCT Pub. Date: May 24, 2012

(65) Prior Publication Data
US 2013/0235898 A1   Sep. 12, 2013

(30) Foreign Application Priority Data
Nov. 18, 2010 (JP) .................. 2010-257844

(51) Int. Cl.
F23D 11/44 (2006.01)
G01N 25/52 (2006.01)

(52) U.S. Cl.
CPC ....... *G01N 25/52* (2013.01); *H01L 2924/0002* (2013.01)

(58) Field of Classification Search
CPC .................................. F21L 17/11; F21L 19/00
USPC ........ 431/353, 247, 207, 253, 234, 310–314
See application file for complete search history.

(56) References Cited

U.S. PATENT DOCUMENTS

| 4,928,605 A * | 5/1990 | Suwa .................. F23D 1/00 110/261 |
| 4,968,402 A | 11/1990 | Kirker et al. |
| 4,976,241 A | 12/1990 | Ishida et al. .................. 123/425 |
| 2004/0220720 A1 | 11/2004 | Noda ............................ 701/111 |
| 2008/0201084 A1 | 8/2008 | Lutnick et al. |
| 2009/0151236 A1 | 6/2009 | Shibata |

(Continued)

FOREIGN PATENT DOCUMENTS

| CA | 1185811 | 4/1985 |
| CN | 101416053 A | 4/2009 |

(Continued)

OTHER PUBLICATIONS

Oshibe, Hlroshi. Makamura, Hlshashi. Tezuka, Takaya. Hasegawa, Susumu. Maruta, Kaoru. "Stabilized three-stage oxidation of DME/air mixture in a micro flow reactor with a controlled temperaure profile". Combustion and FLame. 157. Apr. 9, 2010.*

(Continued)

*Primary Examiner* — Avinash Savani
*Assistant Examiner* — Vivek Shirsat
(74) *Attorney, Agent, or Firm* — Ostrolenk Faber LLP

(57) ABSTRACT

In a combustion experimental apparatus to obtain the positions of flames formed inside a tube (1), it is possible to adjust a temperature gradient in a longitudinal direction applied to the tube, by including a temperature-adjusting fluid supply device (2) to cause a temperature-adjusting fluid to flow along the tube.

11 Claims, 4 Drawing Sheets

(56) References Cited

U.S. PATENT DOCUMENTS

2012/0006316 A1* 1/2012 Shimek .................. F23C 7/004
126/519

FOREIGN PATENT DOCUMENTS

| | | |
|---|---|---|
| DE | 3730046 A1 | 3/1989 |
| EP | 0 318 125 A2 | 5/1989 |
| JP | 2-216439 | 8/1990 |
| JP | 3-269353 | 11/1991 |
| JP | 07-257498 | 10/1995 |
| JP | 10-38470 | 2/1998 |
| JP | 10-142220 | 5/1998 |
| JP | 2004-332584 | 11/2004 |
| JP | 2010-112892 | 5/2010 |
| JP | 2010-216916 | 9/2010 |
| JP | 2011-149739 | 8/2011 |
| JP | 5051659 | 10/2012 |
| JP | 5224118 | 7/2013 |
| KR | 10-1990-0008 | 6/1990 |
| KR | 10-1991-0017262 | 11/1991 |
| KR | 10-1996-0038 | 11/1996 |
| RU | 2 148 826 C1 | 5/2000 |
| RU | 2149880 C1 | 5/2000 |
| RU | 2175131 C1 | 10/2001 |
| RU | 2274851 C2 | 4/2006 |
| RU | 2345359 C2 | 1/2009 |
| RU | 2349573 C2 | 3/2009 |
| SU | 545829 | 3/1977 |
| SU | 1695205 A1 | 11/1991 |
| WO | WO 2009/110509 | 9/2009 |

OTHER PUBLICATIONS

Cengel, Yunus. "Heat Transfer a Practical Approach". pp. 682. McGraw Hill. New York, New York. 2003.*
Office Action dated Feb. 5, 2015 in corresponding U.S. Appl. No. 13/522,357 (9 pages).
Notice of Non-Final Rejection dated Nov. 13, 2013 issued in corresponding. Korean Patent Application No. 10-2012-7019755 (with English language translation).
Official Action dated Nov. 26, 2013 issued in corresponding Russian Patent Application No. 2012134647/15(055371) (with English language translation).
Korean Office Action, dated Jun. 18, 2014, issued in corresponding to Korean Patent Application No. 10-2013-7012410. English translation. Total 9 pages.
Chinese Office Action, dated Jun. 24, 2014, issued in corresponding to Chinese Patent Application No. 20118055191.6. English translation. Total 8 pages.
Russian Decision on Grant, dated Aug. 4, 2014, issued in corresponding Russian Patent Application No. 2013126881/28(039921), date filed Nov. 18, 2011. English Translation. Total 10 pages.
Decision on Refusal dated Jun. 3, 2015 issued in corresponding Russian Patent Application No. 2012134647 with English translation.
Search Report dated Jul. 14, 2015 issued in corresponding European Patent Application No. 10843825.0.
T. Ogura et al., "Modeling of the Oxidation of Primary Reference Fuel in the Presence of Oxygenated Octane Improvers: Ethyl Tert-Butyl Ether and Ethanol", Energy & Fuels, vol. 21, No. 6 (2007) pp. 3233-3239.

R.F. Cracknell et al., "The chemical origin of octane sensitivity in gasoline fuels containing nitroalkanes", Combustion and Flame Elsevier Science Publishing Co., Inc., vol. 156, No. 5, (2008) pp. 1046-1052.
L.J. Kirsch et al., "A Fundamentally Based Model of Knock in the Gasoline Engine", Symposium (International) on Combustion, vol. 16, (1976) pp. 233-244.
Standard Method of Test for Autoignition Temperature of Liquid Petroleum Products, American Society for Testing and Materials D2155-66 (1976) pp. 711-714.
Standard Test Method for Autoignition Temperature of Liquid Chemicals, American Society for Testing and Materials E659-78 (2005) pp. 1-6.
Hiroshi Oshibe, et al., "Study on combustion characteristic of DME in micro flowreactor with temperature control", National Heat Transfer Symposium of Japan Koen Ronbunshu (CD-ROM) (2008) Vol, 45, p. D1510 (with English Abstract).
Russian Office Action, dated Apr. 18, 2014, issued in corresponding Russian Patent Application No. 2013126881/28(039921). English Translation attached. Total 11 pages.
Russian Office Action, dated May 23, 2014, issued in corresponding Russian Patent Application No. 2012134647/15(055371). English Translation attached. Total 13 pages.
Chinese Office Action dated Feb. 11, 2014 issued in corresponding Chinese Patent Application No. 201080061650.7 with English translation.
T. Tsurushima "A new skeletal PRF kinetic model for HCCI combustion", Proceedings of the Combustion Institute (2009), vol. 32, issue 2, pp. 2835-2841.
Kaoru Maruta et al. "Catalytic Combustion in Microchannel for MEMS Power Generation", The Third Asia-Pacific Conference on Combustion, (2001).
Gunther Kolb et al., "A micro-structured 5kW complete fuelprocessor for iso-octane as hydrogen supply system for, mobile auxiliary power units Part II—Development of water-gas shift and preferential oxidation catalysts reactors and assembly of the fuel processor", Chemical Engineering Journal (2008), vol. 138, pp. 474-489.
Wang Zhi et al. "Study of HCCI Combustion Characteristics with High RON Fuel", Transactions of CSICE (2004), vol. 22, No. 1 (English abstract on first page).
Kaoru Maruta et al., "Lower limit of weak flame in a heated channel", Proceedings of the Combustion Institute (2009), vol. 32, pp. 3075-3081.
Search Report dated Aug. 17, 2010 issued in corresponding International Patent Application No. PCT/JP2010/003353 with English translation.
Search Report dated Jan. 10 2012 issued in corresponding International Patent Application No. PCT/JP2011/076681 with English translation.
Jis K 2280-1996 Petroleum Products-Fuels-Determination of Octane Number, Cetane Number and Calculation of Cetane Index (1996) pp. 1084-1149 with partial English translation.
Hisashi Nakamura et al. "Ondo Bunpu Seigyogata Micro Flow Reactor o Mochiita PRF no Jichakka Tokusei" , Proceedings of the Japanese symposium on Combustion (2009) Dai 47 Kai, pp. 234-235 (see attached ISR for concise explanation of relevance).
Hiroshi Oshibe, et al., "Stabilized three-stage oxidation of DME/air mixture in a micro flow reactor with a controlled temperature profile", Combustion and Flame, vol. 157, Apr. 9, 2010.
Akira Yamamoto, et al., "Stabilized three-stage oxidation of gaseous $n$-heptane/air mixture in a micro flow reactor with a controlled temperature profile," Proceedings of the Combustion Institute, vol. 33, No. 2, Aug. 7, 2010, pp. 3259-3266.

* cited by examiner

100 # COMBUSTION EXPERIMENTAL APPARATUS

CROSS-REFERENCE TO RELATED APPLICATIONS

The present application is a 35 U.S.C. §§371 national phase conversion of PCT/JP2011/076681, filed Nov. 18, 2011, which claims priority to Japanese Patent Application No. 2010-257844, filed Nov. 18, 2010, the contents of which are incorporated herein by reference. The PCT International Application was published in the Japanese language.

TECHNICAL FIELD

The present invention relates to a combustion experimental apparatus.

BACKGROUND ART

Conventionally, when measuring an ignition temperature of flammable liquid used as fuel, the so-called ASTM method (American Standard of Testing Method) is used widely. However, in the ASTM method (ASTM D2155-66, ASTM E659-79), since a combustion space is large, measurement errors become large.

On the other hand, in Patent Document 1, a method is proposed, the method of combusting fuel inside a tube to which a temperature gradient in the longitudinal direction thereof is applied, thereby forming flames therein, and of measuring an ignition temperature of the fuel based on the positions of the flames.

DOCUMENT OF RELATED ART

Patent Document

[Patent Document 1] Japanese Unexamined Patent Application, First Publication No. 2010-112892

SUMMARY OF INVENTION

Technical Problem

By the way, in Patent Document 1, when the temperature gradient in the longitudinal direction is applied to a tube, the tube is heated using a heat source disposed in the side of one end of the tube. As a result, distances from the heat source vary in accordance with parts of the tube, and the temperature gradient in which a temperature is high in the side near the heat source and a temperature is low in the side opposite to the heat source is applied to the tube in the longitudinal direction.

However, in order to accurately measure an ignition temperature of fuel, relationships between the formation positions of flames and the tube temperatures at the formation positions of flames have to be obtained correctly. Accordingly, it may be preferable that the temperature gradient in the longitudinal direction applied to the tube be adjusted from the side of an experimenter.

The present invention has been made in view of the above circumstances, and aims to be able to adjust a temperature gradient in a longitudinal direction applied to a tube, in a combustion experimental apparatus to obtain the positions of flames formed inside the tube.

Solution to Problem

The present invention adopts the following configurations as means to solve the above problems.

According to a first invention, a combustion experimental apparatus is provided, the combustion experimental apparatus including: a test tube in which flames are formed, and in which an internal flow path thereof has a diameter less than a flame-quenching distance in a normal temperature; a supply device to supply a premixed gas produced by mixing fuel and oxidizing agent, into the test tube; a flame position-obtaining device to obtain positions of flames inside the test tube; and a temperature-adjusting fluid supply device to cause a temperature-adjusting fluid to flow along the test tube.

According to a second invention, in the first invention, the temperature-adjusting fluid supply device is capable of adjusting a flow volume of the temperature-adjusting fluid.

According to a third invention, in the first or second invention, the test tube is a straight tube disposed so as to extend in a vertical direction, and the temperature-adjusting fluid supply device causes the temperature-adjusting fluid to flow upward from lower.

According to a fourth invention, in any one of the first to third inventions, the temperature-adjusting fluid supply device includes: a fluid-producing part to produce a fluid; a heater to adjust a temperature of the fluid produced by the fluid-producing part, thereby changing the fluid into the temperature-adjusting fluid; and a guide part to guide the temperature-adjusting fluid from one end of the test tube toward the other end thereof.

According to a fifth invention, in the fourth invention, the guide part surrounds the test tube, and includes an opening exposing a measurement range by the flame position-obtaining device in the test tube.

According to a sixth invention, in the fourth invention, the test tube has transparency for light emitted from the flames, the flame position-obtaining device is an imaging device to take images of the test tube from the outside thereof, and the guide part is a tube surrounding the test tube and having transparency for light emitted from the flames.

Effects of Invention

In the present invention, it is configured so that a temperature-adjusting fluid supply device is capable of causing a temperature-adjusting fluid to flow along a test tube.

In addition, by changing a flow volume, a temperature, a flow rate or the like of the temperature-adjusting fluid, it is possible to change the state of heating the test tube.

Consequently, according to the present invention, by changing the flow volume, the temperature, the flow rate or the like of the temperature-adjusting fluid, it is possible to optionally adjust a temperature gradient in the longitudinal direction of the test tube.

In the present invention, the temperature gradient in the longitudinal direction can be applied to the test tube by only causing the temperature-adjusting fluid to flow. Therefore, the temperature gradient in the longitudinal direction can also be applied to the test tube in a high-pressure environment, and the temperature gradient in the longitudinal direction can be adjusted.

For example, in a case of using a hydrogen burner as a heat source to apply the temperature gradient in the longitudinal direction to the test tube, an opposite flow of flames may occur, and it becomes difficult to carry out the combustion experiment of fuel in the high-pressure environment.

In contrast, according to the present invention, it is possible to easily carry out the combustion experiment of fuel in the high-pressure environment.

DESCRIPTION OF EMBODIMENTS

Embodiments of a combustion experimental apparatus relating to the present invention are described below with reference to the drawings. In addition, in the following drawings, the scale of each member is appropriately changed so as to make each member have a recognizable size.

First Embodiment

Figure 1A:
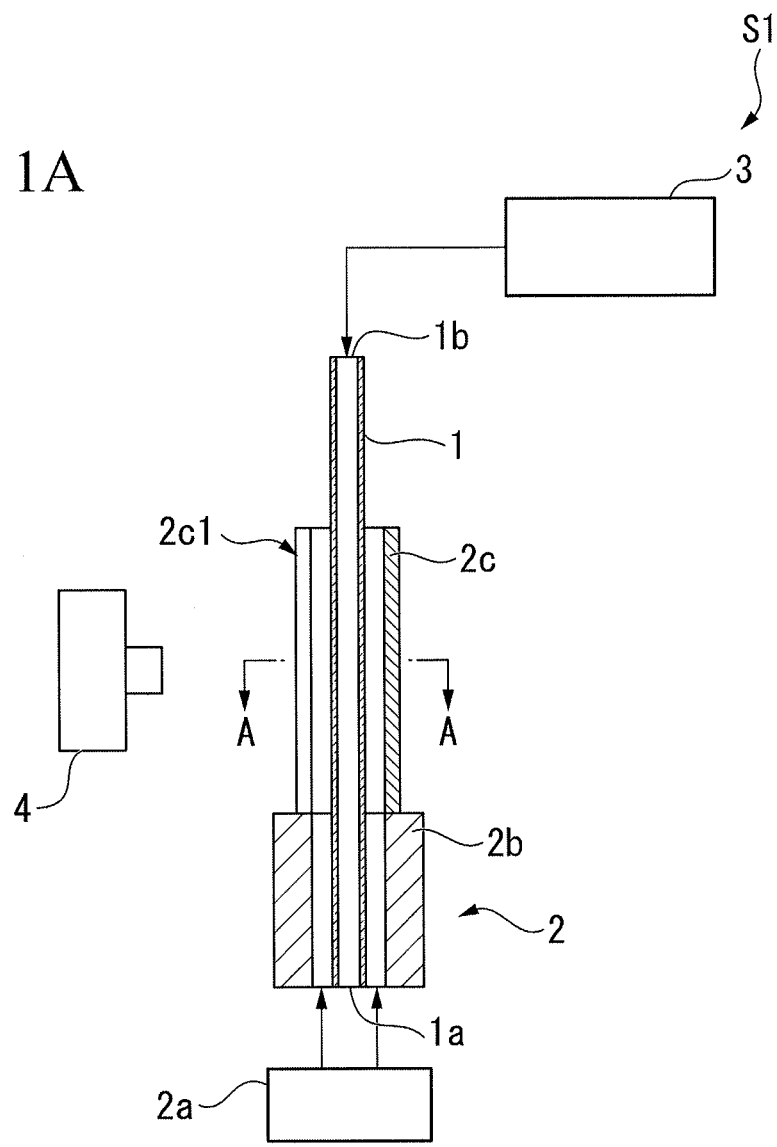
FIG. 1A is a schematic view showing the configuration of a combustion experimental apparatus in a first embodiment of the present invention.
Figure 1B:
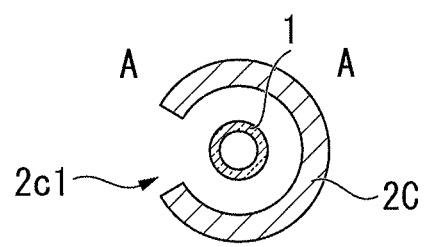
FIG. 1B is a cross-sectional view along line A-A in FIG. 1A.

FIGS. 1A and 1B are schematic views showing the configuration of a combustion experimental apparatus S1 in this embodiment.

The combustion experimental apparatus S1 in this embodiment is an apparatus to combust test evaluation gas containing fuel, thereby forming flames, and to obtain the positions of the flames, when measuring the ignition temperature of the fuel.

As shown in FIG. 1A, the combustion experimental apparatus S1 in this embodiment includes a test tube 1, a temperature-adjusting gas supply portion 2 (temperature-adjusting gas supply device), a test evaluation gas supply portion 3 (supply device), and a camera 4 (flame position-obtaining device).

The test tube 1 is a tube in which flames are formed, and in which the internal flow path thereof has a diameter less than a flame-quenching distance in a normal temperature. In order to transfer flames inside the flow path, the flow path has to have a certain cross-sectional area. If the cross-sectional area of the flow path is small, flames cannot be transferred. In addition, the above flame-quenching distance represents the diameter of a flow path having a cross-sectional area in which formed flames cannot be transferred.

The test tube 1 in the combustion experimental apparatus S1 in this embodiment is a straight tube extending like a straight line, and is arranged so as to extend in the vertical direction by a supporting member (not shown).

In addition, the test tube 1 is formed of materials (for example, quartz glass) having the transparency for the light emitted from flames formed therein.

The temperature-adjusting gas supply portion 2 causes temperature-adjusting gas to flow along the test tube 1 around the test tube 1, thereby applying a temperature gradient in the longitudinal direction to the test tube 1. The temperature-adjusting gas supply portion 2 adjusts the flow volume of the temperature-adjusting gas, thereby adjusting the temperature gradient in the longitudinal direction of the test tube 1.

In addition, the temperature-adjusting gas supply portion 2 injects raw gas constituting the temperature-adjusting gas and forms the flow of the raw gas. That is, the temperature-adjusting gas supply portion 2 corresponds to a fluid-producing part to produce fluid in the present invention.

As shown in FIG. 1A, the temperature-adjusting gas supply portion 2 is disposed in the side of one end 1a of the test tube 1, and includes a fluid injection part 2a, a heater 2b, and a guide part 2c.

As shown in FIG. 1A, the one end 1a of the test tube 1 is formed as an open end, and the one end 1a is surrounded by the heater 2b. The temperature-adjusting gas supply portion 2 injects the raw gas into between the test tube 1 and the heater 2b.

In addition, as the raw gas that is injected from the temperature-adjusting gas supply portion 2, it is preferable that gas having high thermal conductivity be adopted, and for example, helium gas can be used.

The combustion experimental apparatus S1 in this embodiment is configured to be able to adjust the flow volume of the raw gas injected from the temperature-adjusting gas supply portion 2. The flow volume of the raw gas injected from the temperature-adjusting gas supply portion 2 is adjusted, and thereby the flow volume of the temperature-adjusting gas produced by heating the raw gas can be adjusted.

That is, in the combustion experimental apparatus S1 in this embodiment, the temperature-adjusting gas supply portion 2 adjusts the flow volume of the temperature-adjusting gas.

The heater 2b heats the raw gas injected from the temperature-adjusting gas supply portion 2, and adjusts the temperature of the raw gas, thereby changing the raw gas into the temperature-adjusting gas.

The heater 2b in the combustion experimental apparatus S1 in this embodiment is formed in a cylindrical shape, is supported by a supporting member (not shown), and is disposed so as to surround the side of the one end 1a of the test tube 1.

The guide part 2c is connected to the heater 2b, and guides the temperature-adjusting gas produced by heating the raw gas by the heater 2b, along the test tube 1 around the test tube 1.

The guide part 2c is formed of a cylindrical heat-insulating member in which the test tube 1 is enclosed. The length of the guide part 2c is set so that the guide part 2c is disposed over the range in which the camera 4 takes an image. In addition, as shown in the cross-sectional view of FIG. 1B, the guide part 2c includes an opening 2c1 exposing the range in which the camera 4 takes an image, and thereby the cross-sectional shape of the guide part 2c is set into a C-shape.

As shown in FIG. 1A, the test evaluation gas supply portion 3 is connected to the other end 1b of the test tube 1, and supplies the test evaluation gas to the test tube 1.

The test evaluation gas supply portion 3 supplies premixed gas produced by premixing fuel and oxidizing agent, as the test evaluation gas. In addition, the test evaluation gas supply portion 3 heats the test evaluation gas so that the temperature of the test evaluation gas becomes near the temperature of the test tube 1.

The camera 4 is disposed in the lateral side of the test tube 1 by a supporting member (not shown). The camera 4 takes images of the test tube 1, thereby obtaining the positions of flames inside the test tube 1.

In addition, since the amount of light emitted from the flames formed inside the test tube 1 is slight, it is preferable that the camera 4 set an exposure time longer as necessary when taking images.

In the combustion experimental apparatus S1 in this embodiment having the above configuration, the temperature-adjusting gas supply portion 2 supplies the temperature-adjusting gas to around the test tube 1 along the test tube 1, before the test evaluation gas supply portion 3 supplies the test evaluation gas to inside the test tube 1.

In detail, raw gas is injected from the fluid injection part 2a, the raw gas is heated by the heater 2b, thereby changing into the temperature-adjusting gas, and the temperature-adjusting gas is guided by the guide part 2c. Thereby, the temperature-adjusting gas is supplied to around the test tube 1 along the test tube 1.

In this way, by supplying the temperature-adjusting gas to around the test tube 1 along the test tube 1, the test tube 1 is heated by the temperature-adjusting gas.

Naturally, the nearer the heater 2b, the higher the temperature of the temperature-adjusting gas is. Therefore, the temperature of the test tube 1 heated by the temperature-adjusting gas is high in the side of the heater 2b, and is lower gradually as being separated from the heater 2b. As a result, a temperature gradient having a lower temperature gradually as proceeding from the one end 1a of the test tube 1 to the other end 1b thereof is applied to the test tube 1 in the longitudinal direction.

The temperature gradient in the longitudinal direction applied to the test tube 1 can be changed (adjusted) by adjusting the flow volume of the temperature-adjusting gas.

Figure 2:
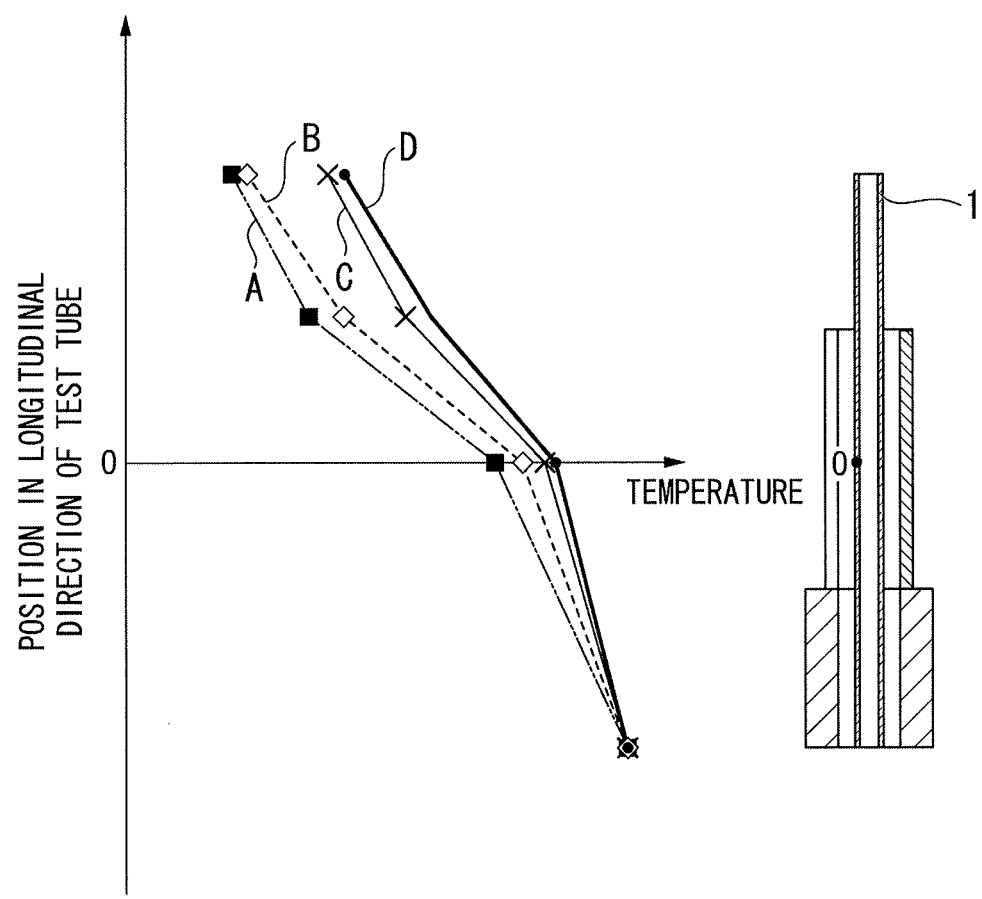
FIG. 2 is a diagram showing temperature gradients in the longitudinal direction of a test tube, in a case where the flow volume of temperature-adjusting gas is changed in the combustion experimental apparatus in the first embodiment of the present invention.

FIG. 2 is a diagram showing temperature gradients in the longitudinal direction applied to the test tube 1, in a case where the flow volume of temperature-adjusting gas is changed. In FIG. 2, the vertical axis represents the position in the test tube 1, and the horizontal axis represents the temperature of the test tube 1. The origin O of the vertical axis in FIG. 2 represents the middle in the longitudinal direction of the test tube 1. In addition, in FIG. 2, a line A represents the result when the flow volume of the temperature-adjusting gas is set the least, and lines B, C, D represent the results when the flow volume of the temperature-adjusting gas are is larger gradually.

In FIG. 2, it is shown that the larger the flow volume of temperature-adjusting gas, the larger the amount of heat transferred to the side of the other end 1b of the test tube 1 and the smaller the temperature gradient in the longitudinal direction of the test tube 1.

In a case of measuring an ignition temperature by using the test tube 1 in the combustion experimental apparatus S1 in this embodiment, a temperature gradient (that is, a temperature distribution) in the longitudinal direction of the test tube 1 has to be measured specially. For example, this measurement can be performed by disposing a thermocouple so as to pass through the test tube 1, in a state where the supply of the test evaluation gas is stopped. The temperature measurement using the thermocouple may be performed before obtaining the formation positions of flames. However, when considering the influence on the test tube 1 by disposing the thermocouple so as to pass therethrough, it is preferable that the temperature measurement be performed after obtaining the formation positions of flames.

Since the difference of the temperature distribution in the longitudinal direction of the flow path of the test tube 1 between cases with flames and without flames is small enough, the difference can be disregarded when carrying out the experiment.

The smaller the temperature gradient in the longitudinal direction of the test tube 1, the smaller the temperature change relative to positional change in the longitudinal direction of the test tube 1. Therefore, the relationships between the positions in the test tube 1 and the temperatures thereof can be obtained accurately, and a correct ignition temperature of fuel can be obtained.

On the other hand, for example, in a case of obtaining the positions of flames in a high-pressure environment by installing the combustion experimental apparatus S1 of this embodiment in the high-pressure environment, it may be preferable that the flow volume of the temperature-adjusting gas be small in order to maintain the high-pressure environment. In this case, in the range in which the high-pressure environment can be maintained, the flow volume of the temperature-adjusting gas is set so that the temperature gradient in the longitudinal direction of the test tube 1 is as small as possible.

In this way, in the combustion experimental apparatus S1 in this embodiment, the flow volume of the temperature-adjusting gas is adjusted based on conditions required to the combustion experiment.

For example, in a diesel engine or a gas engine, fuel is combusted in a high-pressure environment having about 10 MPa at the maximum. Accordingly, in order to obtain combustion characteristics of fuel that is used for the diesel or gas engine, it is preferable that the experiment be carried out in a similar high-pressure environment. Thus, in order to obtain combustion characteristics of fuel in the diesel or gas engine by using a simulation, it is preferable that the experiment be carried out by installing the combustion experimental apparatus S1 of this embodiment in the high-pressure environment having the same conditions as that of the combustion chamber in the diesel or gas engine.

In this way, when the temperature gradient in the longitudinal direction is applied to the test tube 1, subsequently, the test evaluation gas is supplied from the test evaluation gas supply portion 3 to the other end 1b of the test tube 1.

The test evaluation gas which has been supplied to the test tube 1 with the temperature gradient in the longitudinal direction is heated by moving inside the test tube 1, whereby the temperature thereof becomes high. Furthermore, when the test evaluation gas is heated into its ignition temperature or more, the test evaluation gas is ignited. As a result, flames are formed inside the test tube 1.

The formation positions of flames are changed in accordance with the flow volume of the test evaluation gas supplied from the test evaluation gas supply portion 3 to the test tube 1. In addition, if the flow volume of the test evaluation gas supplied to the test tube 1 is large, even when the flow volume is set constant, the formation positions of flames are changed. Accordingly, it is preferable that the flow volume of the test evaluation gas supplied from the test evaluation gas supply portion 3 to the test tube 1 be controlled into a flow volume in which the formation positions of flames are not changed when the flow volume is set constant.

In the combustion experimental apparatus S1 in this embodiment, flames are formed inside the test tube 1 by the above-described way, and the camera 4 takes images, thereby obtaining the formation positions of the flames.

According to the combustion experimental apparatus S1 in this embodiment as described above, it is possible to optionally adjust the flow volume of the temperature-adjusting gas, and to optionally adjust the temperature gradient in the longitudinal direction of the test tube 1. Thereby, it is possible to perform the accurate measurement in the range suitable for the experimental environment.

According to the combustion experimental apparatus S1 in this embodiment, the temperature gradient in the longitudinal direction can be applied to the test tube even in the high-pressure environment, and the temperature gradient in the longitudinal direction can be adjusted. Thereby, even in the high-pressure environment, the combustion experiment of fuel can be carried out easily.

According to the combustion experimental apparatus S1 in this embodiment, heat can be efficiently transferred to the test tube 1 by using the temperature-adjusting gas. For example, compared with a case of using a hydrogen burner, the energy required to apply the temperature gradient in the longitudinal direction to the test tube 1 can be reduced into about 1/100.

Since the energy is reduced, the amount of radiation heat to the surroundings is decreased. Thereby, for example, even if the combustion experimental apparatus S1 in this embodiment is installed in a pressure resistance chamber, the temperature of the pressure resistant chamber can be prevented from being increased.

In the combustion experimental apparatus S1 in this embodiment, the test tube 1 is formed in a straight tube, and is disposed so as to extend in the vertical direction. In addition, the temperature-adjusting gas supply portion 2 causes the temperature-adjusting gas to flow upward from lower.

Therefore, by the natural convection, the temperature-adjusting gas having a high temperature naturally moves upward, and the test evaluation gas having a low temperature moves downward. Consequently, it is possible to reduce the energy to cause the temperature-adjusting gas and the test evaluation gas to flow.

In the combustion experimental apparatus S1 in this embodiment, the guide part 2c to guide the temperature-adjusting gas from the one end 1a of the test tube 1 toward the other end 1b thereof is provided.

Therefore, it is possible to prevent the temperature-adjusting gas from diffusing in the radial direction of the test tube, and to efficiently heat the test tube 1.

In the combustion experimental apparatus S1 in this embodiment, since the guide part 2c is formed of a cylindrical heat-insulating member, it is possible to more efficiently heat the test tube 1.

In addition, in the combustion experimental apparatus S1 in this embodiment, the guide part 2c includes the opening 2c1 exposing the imaging range (measurement range) by the camera 4 in the test tube 1. Therefore, it is possible to reliably obtain the positions of flames.

Second Embodiment

Next, a second embodiment of the present invention is described below. In addition, in the description of this embodiment, the explanations regarding the same parts as that of the first embodiment are omitted or simplified.

Figure 3A:
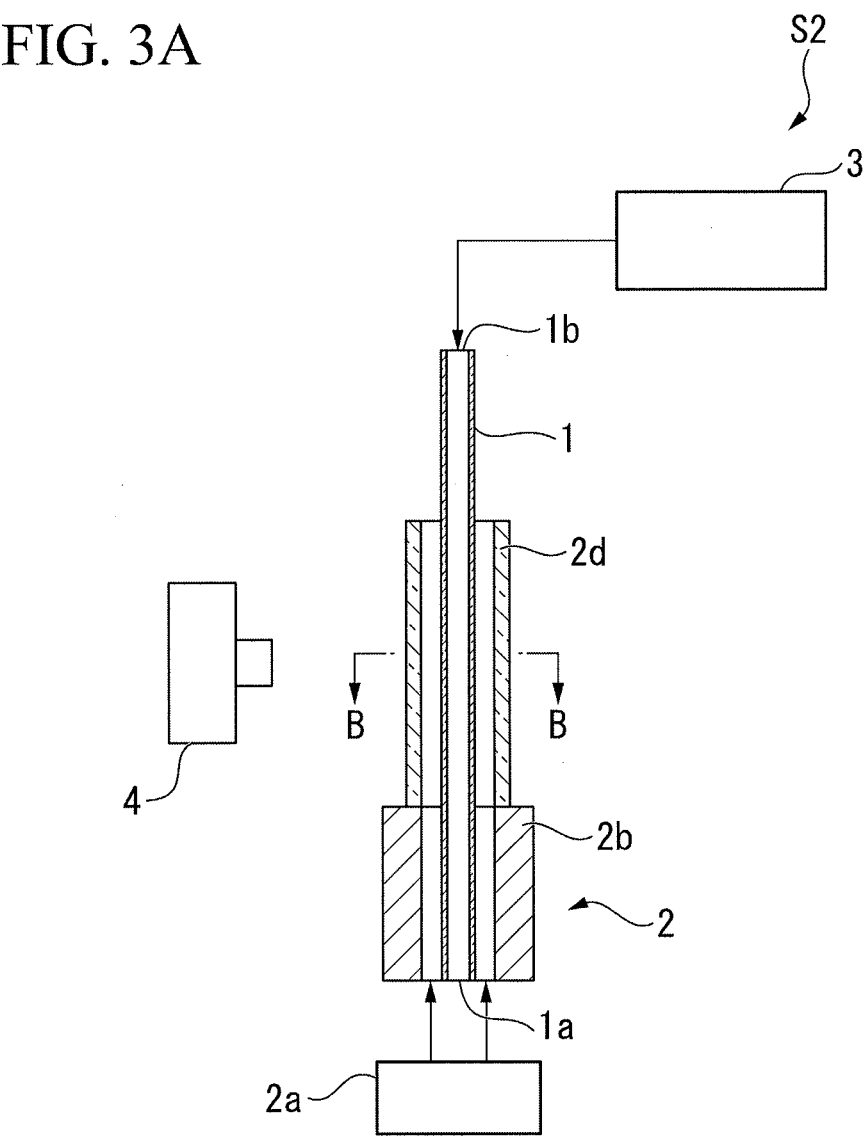
FIG. 3A is a schematic view showing the configuration of a combustion experimental apparatus in a second embodiment of the present invention.
Figure 3B:
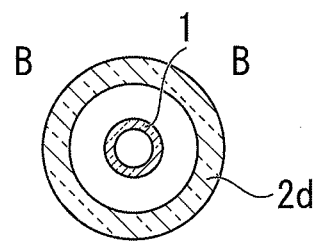
FIG. 3B is a cross-sectional view along line B-B in FIG. 3A.

FIGS. 3A and 3B are schematic views showing the configuration of a combustion experimental apparatus S2 in this embodiment. As shown in these drawings, the combustion experimental apparatus S2 in this embodiment includes a guide part 2d formed of a glass tube (transparent tube) surrounding the test tube 1 and having the transparency for the light emitted from flames, instead of the guide part 2c included in the combustion experimental apparatus S1 in the first embodiment and formed of a cylindrical heat-insulating member.

According to the combustion experimental apparatus S2 in this embodiment adopting the above configuration, since the guide part 2d has the transparency for the light emitted from flames, an opening does not have to be provided in the guide part 2d.

Therefore, the temperature-adjusting gas can uniformly flow around the test tube 1, and the non-uniformity in temperature can be prevented from being caused in the circumferential direction of the test tube 1.

Third Embodiment

Next, a third embodiment of the present invention is described below. In addition, in the description of this embodiment, the explanations regarding the same parts as that of the first embodiment are omitted or simplified.

Figure 4A:
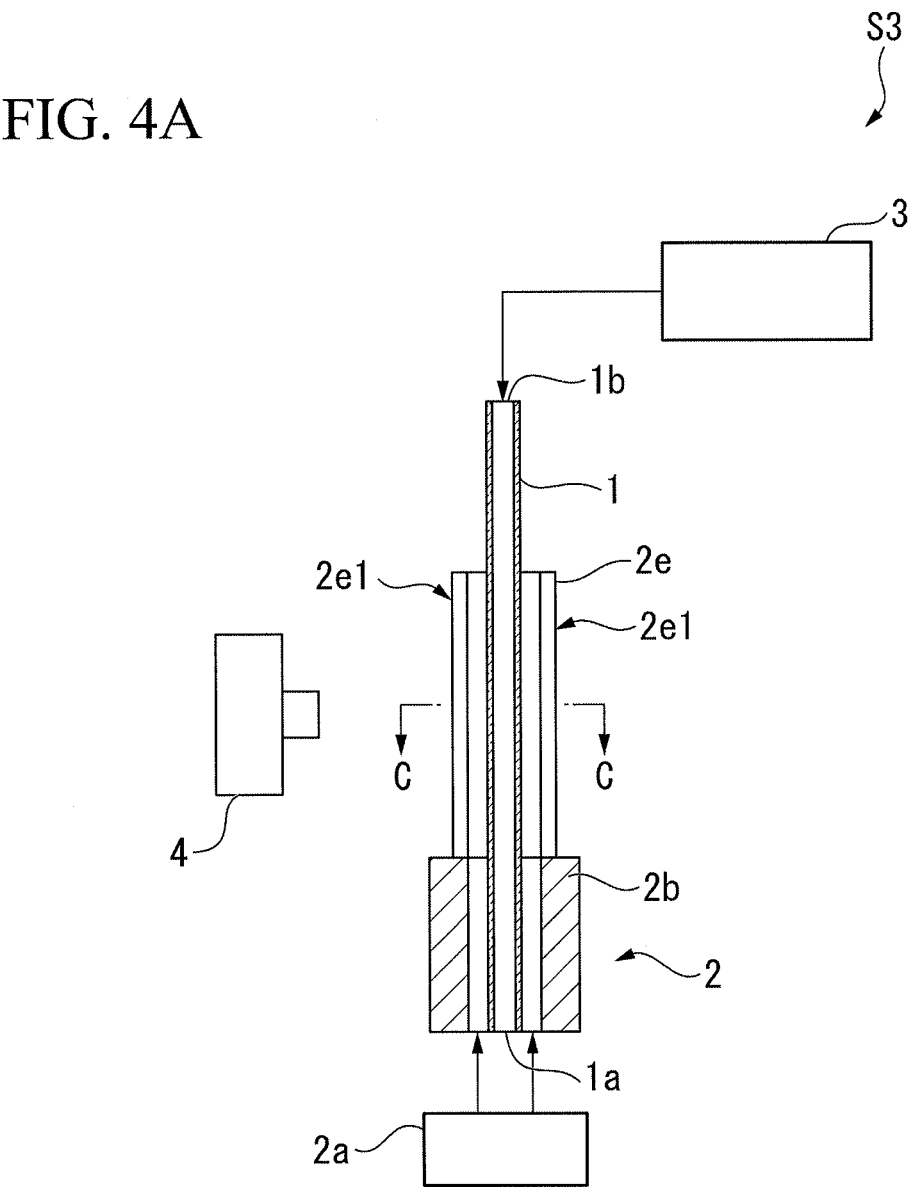
FIG. 4A is a schematic view showing the configuration of a combustion experimental apparatus in a third embodiment of the present invention.
Figure 4B:
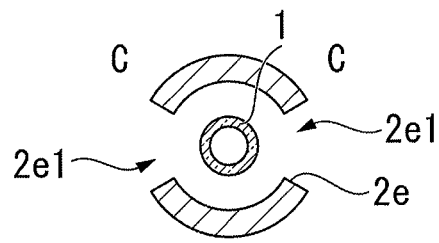
FIG. 4B is a cross-sectional view along line C-C in FIG. 4A.

FIGS. 4A and 4B are schematic views showing the configuration of a combustion experimental apparatus S3 in this embodiment. As shown in these drawings, the combustion experimental apparatus S3 in this embodiment includes a guide part 2e formed of a heat-insulating member and having openings 2e1 each provided in the side of the camera 4 and in the side opposite to the camera 4, instead of the guide part 2c included in the combustion experimental apparatus S1 in the first embodiment and formed of a cylindrical heat-insulating member.

According to the combustion experimental apparatus S3 in this embodiment having the above configuration, the positions of flames can be reliably obtained through the opening 2e1 of the guide part 2e provided in the side of the camera 4.

Furthermore, the guide part 2e is heated similarly to heating the test tube 1, and thereby the guide part 2e may emit light. On the other hand, according to the combustion experimental apparatus S3 in this embodiment, since the opening 2e1 is provided in the guide part 2e in the side opposite to the camera 4, a light-emitting area due to the application of heat to the guide part 2e is not caused in the side behind flames when seen from the camera 4. Therefore, it is possible to more reliably obtain the positions of flames.

Hereinbefore, preferable embodiments of the present invention were described with reference to the drawings, but the invention is not limited to the above-described embodiments. A shape, a combination or the like of each constituent member presented in the above embodiments is illustrative only, and various modifications can be adopted based on a design request or the like within the scope not departing from the gist of the present invention.

For example, in the above embodiments, the configuration was described in which the temperature-adjusting gas supply portion 2 included the fluid injection part 2a, the heater 2b, and the guide part 2c.

However, the present invention is not limited to this configuration. When having a function of causing the temperature-adjusting gas to flow along the test tube 1, the configuration of the temperature-adjusting gas supply portion 2 is not limited particularly.

For example, a configuration in which a heater and a fluid injection part are integrated with each other, a configuration without a heater, or a configuration without a guide part can be adopted.

In the above embodiments, the configuration was described in which the test tube was formed in a straight tube, and was disposed so as to extend in the vertical direction.

However, the present invention is not limited to this configuration. It is possible to use a test tube having a slightly curved shape, or a test tube even formed in a straight tube, and disposed so as to extend in a direction little different from the vertical direction. In this way, in the present invention, a test tube having a slightly curved shape, or a test tube disposed so as to extend in a direction little different from the vertical direction is also called a vertical straight tube.

In the above embodiments, the configuration was described in which the camera was used as a flame position-obtaining device.

However, the present invention is not limited to this configuration. It is possible to use a temperature sensor as the flame position-obtaining device, the temperature sensor capable of measuring a tube wall temperature of a test tube inside which flames are formed, and of determining the positions of the flames based on the measured values.

For example, a controller may be provided, the controller capable of adjusting the flow volume of the temperature-adjusting gas based on instructions from an operating portion, or from a sensor to measure the surrounding environment.

In the above embodiments, the configuration was described in which the temperature gradient in the longitudinal direction applied to the test tube 1 was adjusted by changing the flow volume of the temperature-adjusting gas.

However, the present invention is not limited to this configuration. It is possible to adjust the temperature gradient in the longitudinal direction applied to the test tube 1, by changing the temperature or the flow rate of the temperature-adjusting gas.

INDUSTRIAL APPLICABILITY

According to the present invention, in a combustion experimental apparatus to obtain the positions of flames formed inside a tube, a temperature gradient in a longitudinal direction applied to the tube can be adjusted.

DESCRIPTION OF REFERENCE SIGNS

S1, S2, S3 Combustion experimental apparatus
1 Test tube
1a One end
1b Other end
2 Temperature-adjusting gas supply portion (temperature-adjusting fluid supply device)
2a Fluid injection part (fluid-producing part)
2b Heater
2c Guide part
2c1 Opening
2d Guide part
2e Guide part
2e1 Openings
3 Test evaluation gas supply portion (supply device)
4 Camera (flame position-obtaining device)

The invention claimed is:

1. A combustion experimental apparatus comprising:
    a test tube in which flames are formed and in which an internal flow path thereof has a diameter less than a flame-quenching distance in a normal temperature;
    a supply device to supply a premixed gas produced by mixing fuel and oxidizing agent into the test tube;
    a flame position-obtaining device to obtain positions of flames inside the test tube; and
    a temperature-adjusting fluid supply device to cause a temperature-adjusting fluid to flow along the test tube,
    wherein the temperature-adjusting fluid supply device includes:
        a heater configured to adjust the temperature of a fluid and to change the fluid into the temperature-adjusting fluid; and
        a guide part configured to guide the temperature-adjusting fluid from a first end toward a second end of the test tub;
    wherein the heater is formed into a cylindrical shape surrounding the first end of the test tube,
    wherein the guide part is formed into a tube shape surrounding the test tube, and an end of the guide part in an axial direction thereof contacts an end of the heater in an axial direction thereof, and
    wherein the temperature-adjusting fluid supply device is configured to cause the temperature-adjusting fluid to flow from the first end toward the second end of the test tube through a space between the test tube and the heater and a space between the test tube and the guide part.

2. The combustion experimental apparatus according to claim 1, wherein the temperature-adjusting fluid supply device is capable of adjusting a flow volume of the temperature-adjusting fluid.

3. The combustion experimental apparatus according to claim 1, wherein the test tube is a straight tube disposed so as to extend in a vertical direction, and the temperature-adjusting fluid supply device causes the temperature-adjusting fluid to flow upward from lower.

4. The combustion experimental apparatus according to claim 1, wherein the temperature-adjusting fluid supply device further includes:
    a fluid-producing part to produce the fluid, and
    wherein the heater is configured to adjust the temperature of the fluid produced by the fluid-producing part and to change the fluid into the temperature-adjusting fluid.

5. The combustion experimental apparatus according to claim 1, wherein the guide part surrounds the test tube, and includes an opening exposing a measurement range by the flame position-obtaining device in the test tube.

6. The combustion experimental apparatus according to claim 1, wherein the test tube has transparency for light emitted from the flames, the flame position-obtaining device is an imaging device to take images of the test tube from the outside thereof, and the guide part is a tube surrounding the test tube, and having transparency for light emitted from the flames.

7. The combustion experimental apparatus according to claim 1, wherein the heater is disposed at the first end of the test tube and is configured to adjust the temperature of the temperature-adjusting fluid to a temperature higher than the ignition temperature of the premixed gas, and the supply device is configured to supply the premixed gas having a temperature lower than that of the temperature-adjusting fluid from the second end toward the first end of the test tube.

8. The combustion experimental apparatus according to claim 1, wherein the guide part and the heater are disposed in series in the axial direction of the guide part.

9. The combustion experimental apparatus according to claim 1, wherein the inner diameter of the end of the guide part is the same as the inner diameter of the end of the heater.

10. The combustion experimental apparatus according to claim 1, wherein the end of the guide part coaxially contacts the end of the heater.

11. The combustion experimental apparatus according to claim 5, wherein the opening is continuously provided in a range from a first end to a second end of the guide part in the axial direction thereof.

\* \* \* \* \*